US008705028B2

(12) United States Patent
Osterkamp et al.

(10) Patent No.: US 8,705,028 B2
(45) Date of Patent: Apr. 22, 2014

(54) CONTAINERIZED SYSTEMS

(75) Inventors: Mark A. Osterkamp, Weatherford, TX (US); Kenneth R. Yawn, Weatherford, TX (US); Alan J. Norris, Southlake, TX (US)

(73) Assignee: PaR Systems, Inc., Shoreview, MN (US)

( * ) Notice: Subject to any disclaimer, the term of this patent is extended or adjusted under 35 U.S.C. 154(b) by 131 days.

(21) Appl. No.: 13/205,325

(22) Filed: Aug. 8, 2011

(65) Prior Publication Data

US 2012/0033209 A1 Feb. 9, 2012

Related U.S. Application Data

(60) Provisional application No. 61/371,584, filed on Aug. 6, 2010.

(51) Int. Cl.
*G01N 21/01* (2006.01)

(52) U.S. Cl.
USPC .......................................... 356/244; 356/625

(58) Field of Classification Search
USPC ......... 356/244, 614–625, 607–608, 639–640; 378/57, 197, 198, 88, 90
See application file for complete search history.

(56) References Cited

U.S. PATENT DOCUMENTS

| | | |
|---|---|---|
| 4,129,041 A | 12/1978 | Bicket |
| 4,607,341 A | 8/1986 | Monchalin |
| 4,633,715 A | 1/1987 | Monchalin |
| 4,659,224 A | 4/1987 | Monchalin |
| 4,966,459 A | 10/1990 | Monchalin |
| 5,065,418 A | 11/1991 | Bermbach |
| 5,080,491 A | 1/1992 | Monchalin et al. |
| 5,137,361 A | 8/1992 | Heon et al. |
| 5,402,235 A | 3/1995 | Monchalin |
| 5,608,166 A | 3/1997 | Monchalin et al. |
| 5,680,212 A | 10/1997 | Blouin et al. |
| 5,754,294 A | 5/1998 | Jones et al. |
| 6,057,927 A | 5/2000 | Levesque et al. |

(Continued)

FOREIGN PATENT DOCUMENTS

| | | |
|---|---|---|
| GB | 2444 854 | 6/2008 |
| WO | WO 2009/142974 | 11/2009 |

OTHER PUBLICATIONS

European Search Report of the European Patent Office Patent Office in counterpart foreign application PCT/US2011/046941 filed Aug. 8, 2011.

(Continued)

*Primary Examiner* — Sang Nguyen
(74) *Attorney, Agent, or Firm* — Steven M. Koehler; Westman, Champman & Koehler, P.A.

(57) ABSTRACT

Containerized systems are provided. In one embodiment, a containerized system includes a moveable three-dimensional container, a first generator, a second generator, and a scanner. The first generator is located within the container, and the second generator is located outside of the container. The scanner is mechanically supported by the container and transmits waves received from the first and the second generators. The containerized system optionally includes one or more rails connected to the outside of the container, and the scanner moves along the one or more rails. The containerized system may also include a multi-axes arm that positions the scanner and that is mechanically supported by the container. Furthermore, the containerized system may include an interferometer, an electronics rack, and/or an air conditioning unit.

21 Claims, 7 Drawing Sheets

(56) References Cited

U.S. PATENT DOCUMENTS

Figure 1:
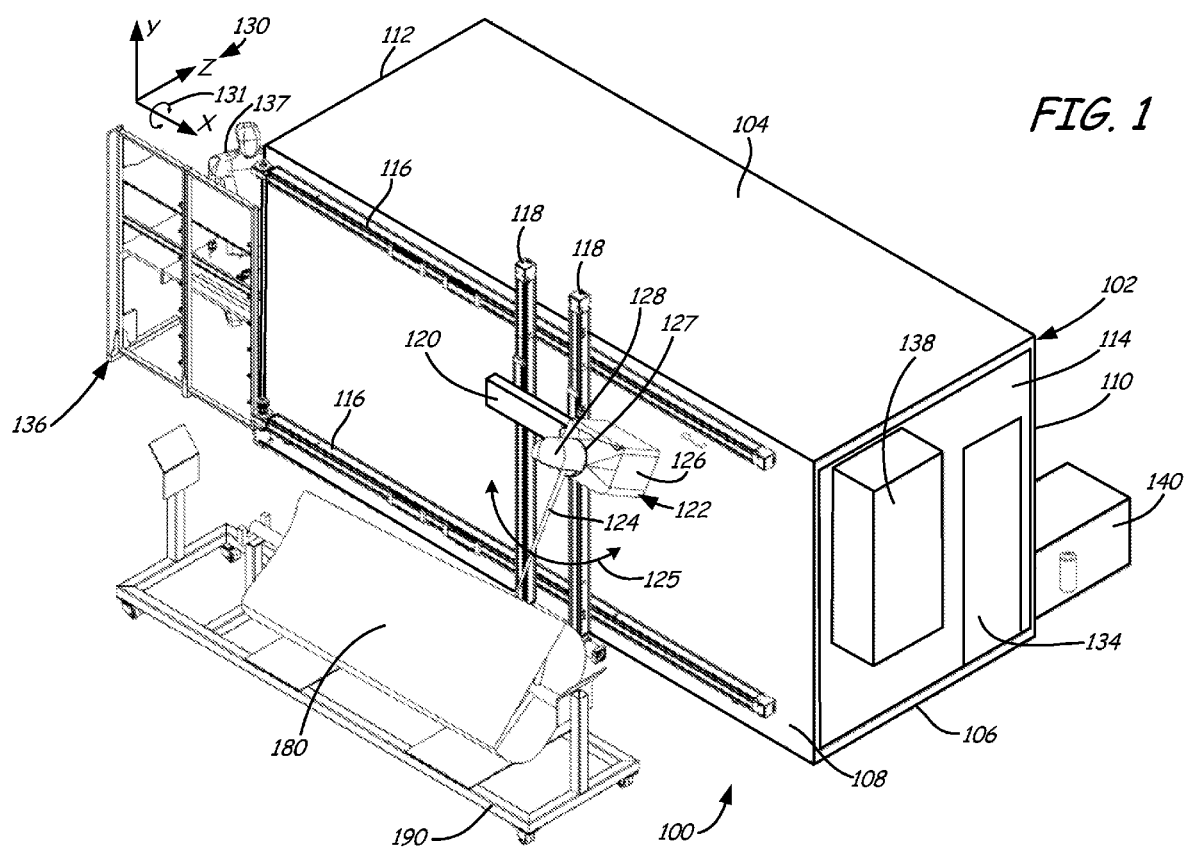

| | | | |
|---|---|---|---|
| 6,094,447 A | 7/2000 | Drake, Jr. | |
| 6,122,060 A | 9/2000 | Drake, Jr. | |
| 6,128,092 A | 10/2000 | Levesque et al. | |
| 6,176,135 B1 | 1/2001 | Dubois et al. | |
| 6,292,533 B1 * | 9/2001 | Swift et al. | 378/57 |
| 6,335,943 B1 | 1/2002 | Lorraine et al. | |
| 6,378,387 B1 | 4/2002 | Froom | |
| 6,483,859 B1 | 11/2002 | Drake, Jr. | |
| 6,571,633 B1 | 6/2003 | Drake, Jr. | |
| 6,606,909 B2 | 8/2003 | Dubois et al. | |
| 6,621,888 B2 * | 9/2003 | Grodzins et al. | 378/57 |
| 6,633,384 B1 | 10/2003 | Drake, Jr. et al. | |
| 6,637,266 B1 | 10/2003 | Froom | |
| 6,643,002 B2 | 11/2003 | Drake, Jr. | |
| 6,649,900 B2 | 11/2003 | Filkins et al. | |
| 6,657,733 B1 | 12/2003 | Drake, Jr. | |
| 6,668,654 B2 | 12/2003 | Dubois et al. | |
| 6,684,701 B2 | 2/2004 | Dubois et al. | |
| 6,700,666 B2 | 3/2004 | Blouin et al. | |
| 6,711,954 B2 | 3/2004 | Drake, Jr. | |
| 6,717,106 B2 * | 4/2004 | Nagano et al. | 219/121.83 |
| 6,732,587 B2 | 5/2004 | Lorraine et al. | |
| 6,763,635 B1 * | 7/2004 | Lowman | 52/114 |
| 6,813,951 B2 | 11/2004 | Blouin et al. | |
| 6,856,918 B2 | 2/2005 | Dubois et al. | |
| 6,873,419 B2 | 3/2005 | Detalle et al. | |
| 7,117,134 B2 | 10/2006 | Dubois et al. | |
| 7,322,745 B2 * | 1/2008 | Agrawal et al. | 378/198 |
| 7,342,665 B2 | 3/2008 | Drake, Jr. | |
| 7,353,709 B2 | 4/2008 | Kruger et al. | |
| 7,369,250 B2 | 5/2008 | Dubois et al. | |
| 7,370,532 B2 | 5/2008 | Osterkamp | |
| 7,418,077 B2 * | 8/2008 | Gray | 378/57 |
| 7,463,363 B2 | 12/2008 | Drake, Jr. et al. | |
| 7,929,664 B2 * | 4/2011 | Goodenough et al. | 378/57 |
| 7,961,094 B2 * | 6/2011 | Breed | 340/541 |
| 8,213,570 B2 * | 7/2012 | Panesar et al. | 378/57 |
| 8,340,245 B2 * | 12/2012 | Herranz et al. | 378/57 |
| 2002/0171845 A1 | 11/2002 | Drake, Jr. | |
| 2002/0171846 A1 | 11/2002 | Drake, Jr. | |
| 2002/0185240 A1 | 12/2002 | Drake, Jr. | |
| 2003/0020923 A1 | 1/2003 | Dubois et al. | |
| 2004/0017887 A1 | 1/2004 | Le | |
| 2004/0247075 A1 | 12/2004 | Johnson | |
| 2005/0099634 A1 | 5/2005 | Dubois et al. | |
| 2005/0231735 A1 | 10/2005 | Dubois et al. | |
| 2005/0281390 A1 | 12/2005 | Johnson | |
| 2006/0132804 A1 | 6/2006 | Dubois et al. | |
| 2006/0262293 A1 * | 11/2006 | Sacher et al. | 356/124 |
| 2008/0016965 A1 | 1/2008 | Drake et al. | |
| 2008/0137105 A1 | 6/2008 | Howard et al. | |
| 2008/0156992 A1 | 7/2008 | Kang | |
| 2008/0181268 A1 | 7/2008 | Dubois et al. | |
| 2008/0291963 A1 | 11/2008 | Deaton, Jr. et al. | |
| 2009/0010285 A1 | 1/2009 | Dubois et al. | |
| 2009/0147920 A1 * | 6/2009 | Barty et al. | 378/88 |
| 2009/0284593 A1 | 11/2009 | Dubois et al. | |
| 2009/0285244 A1 | 11/2009 | Drake, Jr. et al. | |
| 2009/0285523 A1 | 11/2009 | Dubois et al. | |
| 2009/0287427 A1 | 11/2009 | Dubois et al. | |
| 2009/0287450 A1 | 11/2009 | Dubois et al. | |
| 2009/0290163 A1 | 11/2009 | Dubois | |

OTHER PUBLICATIONS

European Search Report and the Written Opinion of the European Patent Office Patent Office in counterpart foreign application No. PCT/US2011/046941 filed Aug. 8, 2011, dated Jan. 27, 2012.

* cited by examiner

CONTAINERIZED SYSTEMS

REFERENCE TO RELATED CASE

The present application is based on and claims the priority of provisional application Ser. No. 61/371,584 filed on Aug. 6, 2010, the content of which is hereby incorporated by reference in its entirety.

BACKGROUND

The discussion below is merely provided for general background information and is not intended to be used as an aid in determining the scope of the claimed subject matter.

Some embodiments of the present disclosure may be used in inspection systems such as, but not limited to, laser ultrasonic inspection systems. In laser ultrasonic inspection systems, a generation system generates an electromagnetic wave (e.g. a wave generated by a $CO_2$ laser) that is directed towards an object that is being inspected (e.g. an item made of a composite material). The generation system wave causes ultrasonic vibrations to occur within the object being inspected. A detection system then generates an electromagnetic wave (e.g. a wave generated by a Nd:YAG laser) that is reflected off from the object being inspected and that is recaptured by the detection system. Changes in phase and/or frequency of the recaptured waves can be used to identify defects in the object. For example, some defects that can be identified include, for illustration purposes only and not by limitation, inclusions, delamination, and porosity.

It should be noted that although certain embodiments of the present disclosure may be described in the context of inspection systems, that embodiments of the present disclosure are not limited to any particular setting and that embodiments may be used in applications and environments that are not associated with inspecting.

SUMMARY

This Summary and the Abstract are provided to introduce some concepts in a simplified form that are further described below in the Detailed Description. The Summary and Abstract are not intended to identify key features or essential features of the claimed subject matter, nor is it intended to be used as an aid in determining the scope of the claimed subject matter. In addition, the description herein provided and the claimed subject matter should not be interpreted as being directed to addressing any of the short-comings discussed in the Background.

An aspect of the disclosure relates to containerized systems. In one embodiment, a containerized system includes a moveable three-dimensional container, a first generator, a second generator, and a scanner. The first generator is located within the container, and the second generator is located outside of the container. The scanner is mechanically supported by the container and transmits waves received from the first and the second generators. The containerized system optionally includes one or more rails connected to the outside of the container, and the scanner moves along the one or more rails. The containerized system may also include a multi-axes arm that is mechanically supported by the container and that positions the scanner. Furthermore, the containerized system may include an interferometer, an electronics rack, an air conditioning unit, and/or modular panels configured to be connected to each other to form a work cell.

In another embodiment, a containerized system includes a moveable three-dimensional container, a generator that is located within the container, a plurality of modular panels connectable to each other to form a work cell, and a scanner that receives waves from the generator and that is located within the work cell. The scanner is optionally supported by either the container or by the work cell. The container may form a portion of the work cell, or the work cell may be formed separately from the container.

In yet another embodiment, a containerized system includes a portable container, a laser generator in the container, a stationary mirror, a travelling minor, and a scanner. The stationary mirror is attached to a fixed position on an outer surface of the container, and the travelling mirror moves along the outer surface of the container. The scanner receives electromagnetic waves that are generated by the laser and reflected by the stationary and travelling mirrors. The containerized system optionally includes a second travelling mirror that moves along the outer surface of the container and that reflects light from the stationary minor to the travelling mirror. The container may comprise a modified shipping container or a custom design trailer. The container may have one or more apertures for transferring gases or heat exchange fluids to the laser generator. The container may also have one or more panels that are interlocked to power down the gas generator, and a carriage that moves the scanner about the outer surface of the container.

Furthermore, a method includes securing a generator within a portable container. The portable container with the generator is transported to an inspection area, and the generator is maintained in a stationary position while an object is inspected with electromagnetic waves produced by the generator. Defects in the object may be identified utilizing an interferometer in the container, and waveforms from the object inspection can be stored in an electronics rack in the container. Additionally, data analysis can be performed utilizing an operations station associated with the container. Some embodiments may utilize a handheld control terminal to read an identifier associated with the object. The object being inspected is illustratively moved utilizing one or more rails, and gas for the generator may be regenerated utilizing a catalyst unit in the container. A work cell may also be formed utilizing modular panels.

In another embodiment of a method, a laser ultrasonic inspection method includes securing a laser generator within a portable container. The portable container is transported to a laser ultrasonic inspection area. The laser generator is maintained in a stationary position while performing a laser ultrasonic inspection of an object with electromagnetic waves produced by the laser generator. Additionally, a work cell may be formed utilizing modular panels, and the laser ultrasonic inspection of the object is performed while the object is in the work cell.

In another embodiment, a laser ultrasonic inspection system includes a moveable three-dimensional container, a gas laser generator that is located within the container, a solid state laser generator that is located outside of the container, and a scanner that is mechanically supported by the container and that transmits waves received from the gas laser generator and the solid state laser generator. The gas laser generator may be a carbon dioxide laser generator, and the solid state laser generator may be a Nd:YAG laser generator or a Yb:YAG laser generator. The system can also include a modular panels configured to be connected together to form a work cell.

Some embodiments may include a motion system having one or more rails. The one or more rails may run horizontally, vertically, or any other direction. A scanner is illustratively carried by a carriage that moves along the one or more rails.

Movement of the carriage and scanner can be accomplished through drive assemblies such as, but not limited to, actuators (e.g. hydraulic, pneumatic, or electric), electric linear motors, conveyor mechanisms, ball screw actuators, or pinion gears driven on racks provided on the one or more rails.

A scanner illustratively transmits and receives electromagnetic waves to inspect an object. The electromagnetic waves can include waves having any wavelengths (e.g. gamma rays, X rays, ultraviolet, visible spectrum, infrared, microwave, radio frequency, and long radio waves). The waves may also include waves other than electromagnetic waves such as, but not limited to, sound waves, sonar, ultrasonic, and subsonic waves. Alternatively, a scanner may not transmit and receive waves, but may instead transmit and/or receive materials (e.g. liquid, gas, particles, etc.).

An object being inspected may be held in place utilizing an object holder. The object holder can hold an object in a fixed position, or may move the object in one or more directions (e.g. along the x-axis, y-axis, and/or z-axis) and/or may rotate the object about one or more axes (e.g. rotate about the x-axis, y-axis, and/or z-axis). Movement of the object holder, and thus the object, can be accomplished through any type of device such as, but not limited to, actuators (e.g. hydraulic, pneumatic, or electric), electric linear motors, conveyor mechanisms, ball screw actuators, or pinion gears driven on racks provided on one or more rails. The movement of the object holder can be synchronized with movement of the scanner such that the system knows which location/area of the object is currently being scanned, and the scanner is able to inspect all desired portion or every portion, if desired, of the object being inspected.

A container may include one or more doors or panels that provide access to any equipment within the container. A container may also include one or more windows to view the equipment within the container. A container door and the size of the container are optionally sized to allow for a human being to enter the containerized system and move around in an upright fashion. A container can include safety interlocks on its doors and/or panels such that no potentially dangerous electromagnetic waves are generated upon a door or panel being opened or removed. Similarly, any windows included within container are optionally tinted or are made from a material such that no potentially dangerous electromagnetic waves (e.g. laser light) are emitted.

A containerized system may also include an HVAC or air conditioning unit and one or more heat exchange units or chillers. The air conditioning unit illustratively controls the temperature and/or the humidity of air entering the container. For instance, an air conditioning unit may cool, heat, dehumidify, and/or humidify air entering the container. An air conditioning unit may also include one or more filters to remove particulate and/or chemical contamination from entering the container. Chillers are illustratively used to cool one or more components of the system. For instance, in one embodiment, a system includes three chillers. Two of the chillers are used to control the temperature of an electromagnetic wave generator associated with a generation system (e.g. a CO2 laser generator), and the third chiller is used to control the temperature of an electromagnetic generator associated with a detection system (e.g. a Nd:YAG or Yb:YAG laser generator). Other embodiments may include any number of chillers including none.

A containerized system may include an operations station. An operations station illustratively includes equipment that enables a user to control operations of the system. For instance, a user may use equipment within the station to perform real-time data analysis, to set-up the system to inspect an object, to review the results of an inspection, or to review any maintenance requirements.

A container is illustratively moveable such that it, and any equipment included within it, can be relocated to a different location. In one embodiment, a container has a rectangular prism shape and includes a top panel, a bottom panel, a front panel, a back panel, a first side panel, and a second side panel. Embodiments are not however limited to any particular shape or any number of panels, and embodiments include any shape and number of panels. For example, in other embodiments, a portable container may be shaped as a cube, a pyramid, a cylinder, or any other three-dimensional shape. In certain embodiments, a container is formed as a modified shipping container, a custom design trailer, or any other type of shelter that can be moved from one location to another.

In an embodiment, the components within a container are illustratively securely attached to or mounted within the container such that the container and the components within it can be moved without any of the components being damaged or without any of the components needing to be uninstalled and reinstalled. Additionally, the container and the components within container are illustratively secured in a fixed or stationary position such that they do not move during operations of the system (e.g. a container and a generator do not move while an object is being inspected).

A container optionally includes a generation system electromagnetic wave generator, a side arm catalyst unit, an interferometer, and electronics rack. A generation system generator illustratively generates waves that are used to cause ultrasonic vibrations in an object that is being inspected. In one embodiment, a generator is a gas laser generator. For instance, the generator may be a carbon dioxide (i.e. $CO_2$) laser generator that generates electromagnetic waves having wavelengths centered at approximately 9.4 to 10.6 micrometers. In another embodiment, the generator is a mid-infrared generator that generates electromagnetic waves centered at approximately 3 to 8 micrometers. Embodiments are not however limited to any particular type of generator and illustratively include any type of generator that produces electromagnetic waves.

A sidearm catalyst unit is utilized by a generator in generating electromagnetic waves. In one embodiment, a catalyst unit is a carbon dioxide catalyst that helps to regenerate a carbon dioxide laser gas mix. Catalyst unit may however include other types of catalyst as needed to support the generation of electromagnetic waves by a generator. Additionally, a catalyst unit does not necessarily need to include any type of catalyst and may instead be another type of supporting equipment that helps a generator generate waves.

An interferometer illustratively receives electromagnetic waves reflected or scattered from an object being inspected. For instance, in one embodiment, a scanner transmits a first electromagnetic wave to an object. The first electromagnetic wave causes ultrasonic vibrations to occur within the object. The scanner then transmits a second electromagnetic wave (e.g. a wave generated by an Nd:YAG or Yb:YAG laser generator) that is reflected off from the object and is recaptured by the scanner. The recaptured waves are transmitted to the interferometer that is able to detect changes in phase and/or frequency of the recaptured waves. The changes in phase and/or frequency can be used to identify defects in the object such as, but not limited to, inclusions, delamination, and porosity.

In one example, for illustration purposes only and not by limitation, an interferometer is a confocal Fabry-Perot interferometer. The Fabry-Perot interferometer has sensitivity for frequencies between 0.5 to 15 megahertz and is able to handle rough surfaces. The Fabry-Perot interferometer is a homodyne interferometer having two mirrors that form a resonant cavity that analyzes the phase and the frequency of the reflected wave. In one implementation, the Fabry-Perot interferometer has two spherical minors spaced approximately 1 meter apart, and the interferometer outputs a wave that reflects back and forth approximately ten to one hundred times within the cavity of the interferometer. This implementation can be configured to reject common-node amplitude noise produced by differences/imperfections in wavelengths and/or frequencies of the wave that is being reflected from the object that is being inspected.

An electronics rack within a container includes any type of electronics that are needed or are useful in supporting the operations of a containerized system. Some examples of electronics that may be included are a computing system (e.g. PC or server), a data archive or database for storing and retrieving inspection information, defect detection analysis hardware and/or software, an uninterrupted power supply, communications interfaces (e.g. wireless transmitter/receiver), one or more controllers, and/or power supplies/conditioners. In one embodiment, a computing system of electronics rack includes a data acquisition and control subsystem, a data visualization subsystem, and a data management subsystem. Waveforms (e.g. ultrasonic waveforms from an interferometer) are digitally captured, processed, and stored while the inspection area/point is indexed over the surface of the object that is being inspected (e.g. a composite surface). Real-time data analysis and visualization tools are available to the user that may decrease time required for inspection and/or analysis processes. The data management is optionally performed with an automated archival system and a database such as, but not limited to, a SQL server database.

In addition to the components included within a container, a system may also include one or more components outside of or partially outside of the container. These components may be securely attached to a container such that they can be moved along with the container, or alternatively, the components may be detachable such that they can be removed before moving. Some examples of outside or partially outside components include an air conditioning unit and one or more chillers. The outside components may also include one or more gas tanks. Gas tanks supply gases to components of the system such as to an electromagnetic wave generator. For instance, tanks may include carbon dioxide (i.e. CO2), nitrogen (N2), hydrogen (H2), carbon monoxide (CO) and helium (He) gases that are used as gas supplies for a CO2 laser generator. Embodiments are of course not limited to any particular implementation and illustratively include any number and types of gases including none.

In an embodiment, a container includes one or more apertures and/or connection points such that gases, cooling lines, and air (e.g. from gas tanks, chillers, and/or A/C unit) may be exchanged between outside components and the components within the container. These apertures and/or connection points are illustratively sealed such that no dangerous electromagnetic waves escape from the container and such that the connections can be at least relatively easily connected/disconnected so that containerized system is moveable.

A containerized system optionally includes a work cell that surrounds or partially surrounds the object that is being inspected. The walls or panels of the cell can be of a permanent nature or, in a particularly advantageous form, the walls or panels can be of a temporary or moveable form. In addition to the side walls, a work cell may also include one or both of a bottom/floor panel and a top/ceiling panel. The top/ceiling panel is illustratively a continuous surface that fully covers the entirety of the top of the work cell. It should also be noted that embodiments of work cell are not limited to any particular shape. For instance, a work cell may have four to six panels that form a rectangular prism shape, or embodiments of work cells may include any number of panels to form any shape.

In one embodiment, the front panel of a container is separate from (i.e. does not form a part of) the work cell. In another embodiment, a container and a work cell hare one or more walls. For instance, a front panel can be used to form one of the walls of work cell, or one of the work cell panels can be used to form one of the walls of the container. Panels are illustratively joined together along the vertices of the work cell. In one embodiment, panels are joined together utilizing any suitable fasteners. Additionally, panels may optionally include seals along the intersections of adjoining panels. Accordingly, panels can be joined together in such a manner as to prevent electromagnetic waves from escaping the interior portion of a work cell. The bottom/floor panel and/or the top/ceiling panel can similarly be joined to panels utilizing suitable fasteners and/or seals to prevent electromagnetic waves from escaping the interior portion of a work cell.

A work cell may also have one or more doors/access panels and/or one or more windows. The work cell can illustratively include safety features that are the same or similar to those of a container. For instance, a work cell may include interlocks on its panels and/or doors to de-energize equipment such that dangerous electromagnetic waves cannot be generated if the interlocks are opened. Also for instance, the cell and any windows may be tinted or made of such a material such that dangerous electromagnetic waves cannot be emitted from the work cell. Furthermore, in one embodiment, the work cell can be constructed of modular panels that are shipped with the container and that are designed to be attached thereto and/or to each other.

An operations station illustratively provides an area in which a user can operate the components of a system. A station may include a monitor and/or input devices (e.g. scroll-ball, keyboard, mouse, touchscreen) that communicates with electronics (e.g. a computer) within an electronics rack. The communications may be wireless or may be through a wired connection through an aperture in a container. In an embodiment, a user can utilize the equipment within station to perform real-time data analysis, visualization, and/or any of the other tasks. An operator can also illustratively utilize the equipment within the station to set-up the system to inspect an object, to review the results of an inspection, to review/monitor any maintenance requirements, etc.

A system also optionally includes a wireless handheld control terminal that is wirelessly communicatively coupled to one or more of electronics rack and/or equipment within operations station. In an embodiment, a wireless handheld control terminal includes a reader (e.g. an optical barcode reader or an RFID reader) that reads an identifier (e.g. a one-dimensional barcode, a two-dimensional barcode, or an RFID tag) on an object that is to be inspected. Handheld control terminal illustratively has a graphical interface that provides instructions and/or feedback to a scanner. For instance, the graphical interface can show whether a barcode was or was not successfully read. Handheld control terminal may be implemented utilizing a computing device such as, but not limited to, a laptop computer, a netbook, a tablet computer, or a smartphone. Handheld control terminal is not however limited to any particular device and can be implemented utilizing any suitable device.

A handheld control terminal illustratively reads an identifier on an object and then attempts to retrieve positioning information for that part. For example, the object may have been previously taught to the system such that the system knows the coordinates/dimensions of the part (e.g. coordinates/dimensions stored in a database of electronics rack). If the object has been taught to the system, the system continues with the inspection process. If the object has not been taught to the system (e.g. the system does not have coordinate/dimension information for the object), then the terminal allows the user to teach the object and store the information to a computing device (e.g. a database within an electronics rack). The stored teach information can then be recalled as necessary. For instance, the stored teach information can be recalled the next time when an object having the same or a similar shape is inspected.

A handheld control terminal may also include other features. In one embodiment, a terminal provides capabilities to control robots/motion systems within a system, to control electromagnetic wave generators, to control interferometer, and to control any other components that may be included within the system and/or communicatively coupled to the system.

A minor configuration can be used to direct an electromagnetic wave from a generator to a scanner. In an embodiment, an electromagnetic wave travels outward from a container along the z-axis through a suitable aperture with or without a covering allowing transmission there through. The wave is then redirected (e.g. reflected) by a stationary minor along the x-axis towards a first travelling mirror. First travelling minor is illustratively attached to vertical rails such that it moves along with the vertical rails. From the first travelling mirror, the wave is then directed upwards along the y-axis towards a second travelling mirror. Second travelling minor is illustratively attached to a carriage such that it moves along with the carriage. The wave is then directed by the second travelling mirror along the x-axis towards scanner. The carriage is optionally hollow or has an aperture that enables the wave to travel from the minor to the scanner.

In one embodiment, a wave is a two and a half inch diameter beam from a carbon dioxide laser. Embodiments are not however limited to any particular type or size of electromagnetic waves and can include any type and size of electromagnetic wave. Additionally, it should be noted that minors do not necessarily need to be mirrors. Minors can for instance be any type of redirecting device. For example, one or more of the mirrors could be implemented using a prism instead of a minor. Furthermore, embodiments of the present disclosure are not limited to any particular configuration of mirrors/redirecting devices and can include other configurations as necessary to redirect a wave from a generator to scanner.

A containerized system may include a first motor attached to a horizontal rails, and a second motor attached to a vertical rails. The first motor has a rotatable output shaft. The motor and shaft rotate bands that run along the horizontal rails and that are attached to vertical rails. Accordingly, as the first motor and its shaft rotate clockwise or counterclockwise, the bands move the vertical rails along the horizontal rails. Similarly, a second motor has a rotatable output shaft. The second motor and its shaft rotate bands that run along the vertical rails and that are attached to a carriage. Accordingly, as the second motor and shaft rotate clockwise or counterclockwise, bands move carriage along the vertical rails.

Embodiments of the present disclosure are not limited to any particular methods of supplying motion or positioning capabilities to a scanner. For instance, embodiments may utilize actuators (e.g. hydraulic, pneumatic, or electric), electric linear motors, conveyor mechanisms, ball screw actuators, or pinion gears driven on racks provided on rails. Furthermore, a system does not necessarily need to have any rails. For example, in another embodiment, a scanner is positioned utilizing one or more multi-axes robots or any other suitable device. It should also be noted that the rails, multi-axes robot, etc. that are used to position a scanner, do not necessarily need to be supported by the container. In another embodiment, the rails, multi-axes robot, etc. are self-supporting and do not need to be attached to or supported by a container. In yet another embodiment, the rails, multi-axes robot, etc. are supported by one or more walls of a work cell. Accordingly, embodiments provide flexibility in which motion can be provided to a scanner.

Embodiments of the present disclosure are also not limited to any particular layout. For instance, the object that is being inspected is outside of the container. In another embodiment, the inspection of objects is performed within the container. In such a case, the container is sized such that components such as scanner, object holder, and rails can be placed within the container. Additionally, an operations station, can also be located within a container, and the container may optionally have one or more suitable partitions to isolate the operations station from any generation system and/or object inspection area. Furthermore, any supporting components such as gas tanks, chillers, HVAC unit, may also be placed within a container. Therefore, embodiments of the present disclosure include different options for layout configurations, which may provide further flexibility for installing, relocating, and/or operating a containerized system.

Embodiments of the present disclosure are not limited to any particular sizes. For instance, although some embodiments include a container that is of suitable size for containing a human within, other embodiments can include a housing of size to contain one or more of the components herein described, but not be of size to accommodate a human. This construction, of whatever size, is particularly beneficial for containerized systems herein described.

In one embodiment, a containerized system does not include any horizontal rails on its front panel. Instead, the front panel illustratively only includes one or more vertical rails. In one embodiment, a system includes a motor that is attached to one of the vertical rails and that has a rotatable output shaft. The motor and shaft rotate bands that run along the vertical rails and that are attached to a carriage. Accordingly, as motor and shaft rotate clockwise or counterclockwise, bands move carriage and scanner up and down along the y-axis.

An object holder may also include one or more rails for providing motion to the object that is being inspected. In one embodiment, an object holder includes one or more rails that run along the x-axis of a coordinate system, and one or more rails that run along the z-axis of a coordinate system. A motor having a rotatable output shaft is attached to one of the rails. The motor and shaft rotate bands that run along rails and that are attached to rails. Accordingly, as motor and shaft rotate clockwise or counterclockwise, bands move the object holder platform, and thus object, side to side along the x-axis of coordinate system.

An object holder may similarly have a second motor having a rotatable output shaft that is attached to another one of the rails. The second motor and shaft rotate bands that run along rails and that are attached to object holder platform. Accordingly, as the second motor and shaft rotate clockwise or counterclockwise, bands move the object holder platform, and thus the object being inspected, back and forth along the z-axis of a coordinate system. Additionally, in one embodiment, object holder platform may be rotatable about the y-axis of a coordinate system by separately adjusting the bands.

Embodiments of the present disclosure are not however limited to any particular methods or components for moving or positioning a scanner and/or an object holder platform. For instance, movement of a scanner and/or a platform can be accomplished through any type of device such as, but not limited to, actuators (e.g. hydraulic, pneumatic, or electric), electric linear motors, conveyor mechanisms, ball screw actuators, or pinion gears driven on racks. Furthermore, movement of an object holder can be synchronized with movement of scanner such that the system knows which location/area of object is currently being scanned, and the scanner is able to inspect every portion of the object being inspected.

A minor configuration can be used for example to direct an electromagnetic wave from a generator to a scanner. In an embodiment, an electromagnetic wave travels outward from container along the z-axis of a coordinate system. The wave is then redirected (e.g. reflected) by a stationary minor along the y-axis towards a travelling minor. Travelling mirror is illustratively attached to a carriage such that it moves along with the carriage. From the travelling minor, a wave is then directed along the x-axis towards the scanner. The carriage is optionally hollow or has an aperture that enables wave to travel from minor to scanner. It should be noted that mirrors do not necessarily need to be mirrors. Mirrors can for instance be any type of redirecting device. For example, one or more of minors could be implemented using a prism instead of a minor. Furthermore, embodiments of the present disclosure are not limited to any particular configuration of mirrors/redirecting devices and can include other configurations as necessary to redirect a wave from a generator to a scanner.

A containerized system may include a scanner head that is connected to a scanner body through a pivot joint. A system also includes a container that is connected to the scanner body through a scanner positioning system. In an embodiment, a system includes a generation system that generates a first electromagnetic wave and a detection system that generates a second magnetic wave. The first electromagnetic wave is illustratively generated by a generation system generator. The generation system generator may be a gas laser generator (e.g. a CO2 generator) or any other type of generator (e.g. gas laser generator, solid state laser generator, etc.). The generator is optionally located within the container. The generator could however be located at other locations within the system such as within the scanner body. From the generator, the generation system electromagnetic wave is illustratively transferred through optics within scanner body to a generation system transmitter in the scanner head. From the transmitter, the generation system electromagnetic wave is illustratively directed to an object that is being inspected (e.g. a composite material). The generation system wave in one embodiment causes ultrasonic vibrations to occur within the object.

A second electromagnetic wave is illustratively generated by a detection system generator. The generator may be a solid state generator (e.g. a Nd:YAG or Yb:YAG laser generator) or any other type of generator (e.g. a gas laser generator, etc.). Generator is optionally located within the scanner body. The generator could however be located at other locations within the system such as within container. From the generator, the detection system electromagnetic wave is illustratively transferred through optics within scanner body to a detection system transmitter in the scanner head. From the transmitter, the detection system electromagnetic wave is illustratively directed to the object being inspected.

The detection system electromagnetic wave is then reflected or redirected by the object being inspected, and is recaptured or received by the detection system receiver in scanner head. The recaptured detection system wave is then optionally transferred through optics in scanner body to an interferometer in container. The interferometer is illustratively able to detect changes in phase and/or frequency of the recaptured waves, and can use those detected changes to identify defects in the object being inspected.

A scanner head may include a galvanometer that can be used to further position generation system transmitter, detection system transmitter, and/or detection system receiver. In one embodiment, a galvanometer is a two-dimensional galvanometer that moves the transmitted electromagnetic waves along two-dimensions. For instance, the two-dimensional galvanometer may have two scanning mirrors that enable movement of +/−10.5° mechanically and +/−21° optically along each of the two axes.

A scanner head and/or scanner body may also contain any other components that may be necessary or desirable. For instance, a scanner head and body may include additional electrical, fiber optic, or other type of cabling. The scanner head and body may also include any number of additional optical or mechanical components for transmitting or redirecting electromagnetic waves. Furthermore, embodiments may include safety covers or dust covers for any of the electromagnetic waves.

A work cell may have one or more doors/access panels and/or one or more windows (e.g. laser safe windows). The work cell can illustratively include safety features that are the same or similar to those of container. For instance, the work cell may include interlocks on its panels and/or doors to de-energize equipment such that dangerous electromagnetic waves cannot be generated if the interlocks are opened. In one embodiment, a work cell optionally includes one or more laser status indicators. For instance, a work cell may include a laser status indicator at each entrance. The status indicator could for example indicate to a user whether or not a laser is active or not. This could be useful in preventing a user from walking into a work cell when the laser is turned on. Additionally, the doors to the work cell may be interlocked such that the laser is de-activated (i.e. waves are not generated) when a door is opened.

A work cell can be constructed of modular panels that are shipped with the container and that are designed to be attached thereto and/or to each other. The modular panels may be rigid panels. Alternatively, one or more of the panels may be flexible panels (e.g. like a curtain, etc.). For instance, all of the panels of a work cell may be flexible panels, or a portion of the panels of a work cell may be flexible panels, and the remainder of the panels are rigid.

In an embodiment, the object that is being inspected is outside of the container. In another embodiment, the inspection of objects is performed within the container. In such a case, the container is sized such that components such as a scanner, an object holder, and rails can be placed within the container. Additionally, an operations station, can also be located within a container, and the container may optionally have one or more suitable partitions to isolate the operations station from any generation system and/or object inspection area. Furthermore, any supporting components such as gas tanks, chillers, HVAC unit, may also be placed within container. Therefore, embodiments of the present disclosure include different options for layout configurations, which may provide further flexibility for installing, relocating, and/or operating a containerized system.

Another possible layout, for illustration purposes only and not by limitation, includes placing everything within the moveable container. For example, the operations station, the work cell (i.e. object inspection area), supporting components (e.g. gas tanks, chillers, etc.), the scanner, and the scanner positioning system are illustratively all placed within a moveable container. In another possible layout, the operations station is placed within a moveable container, but the work cell (e.g. the object inspection area) is placed outside of the moveable container. These other layouts may provide further options for incorporating a containerized system in an operating environment.

A system controller may be used in a containerized system (e.g. in an electronics rack, operations station, and/or handheld control terminal). A system controller comprises a conventional computer having a central processing unit (CPU), memory, and a system bus, which couples various system components, including memory to the CPU. The system bus may be any of several types of bus structures including a memory bus or a memory controller, a peripheral bus, and a local bus using any of a variety of bus architectures. The memory includes read only memory (ROM) and random access memory (RAM). A basic input/output (BIOS) containing the basic routine that helps to transfer information between elements within the controller, such as during startup, is stored in ROM. Storage devices, such as a magnetic, optical, solid state, or polymer-based storage systems are coupled to the system bus and are used for storage of programs and data. Commonly, programs are loaded into memory from at least one of the storage devices with or without accompanying data.

Input devices such as a keyboard, pointing device (e.g. mouse), or the like, allow the user to provide commands to the controller. A monitor or other type of output device is further connected to the system bus via a suitable interface and provides feedback to the user. If the monitor is a touch screen, the pointing device can be incorporated therewith. The monitor and typically an input pointing device such as mouse together with corresponding software drivers form an interface (e.g. a graphical user interface) for the controller. Interface(s) allow communication between system controller and other system components. Interface(s) also represent circuitry used to send and receive signals. Commonly, such circuitry comprises digital-to-analog (D/A) and analog-to-digital (A/D) converters as is well known in the art.

These and various other features and advantages that characterize the claimed embodiments will become apparent upon reading the following detailed description and upon reviewing the associated drawings.

BRIEF DESCRIPTIONS OF THE DRAWINGS

Figure 2:
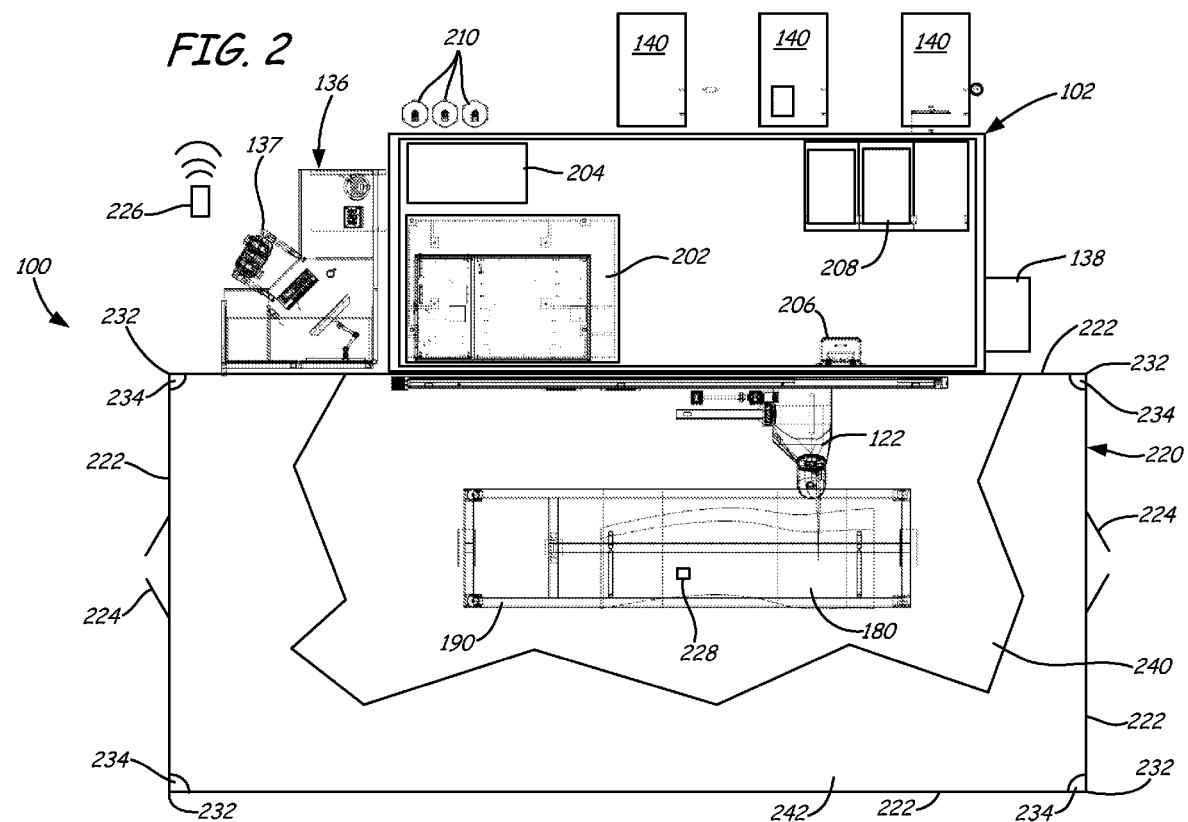
Figure 3:
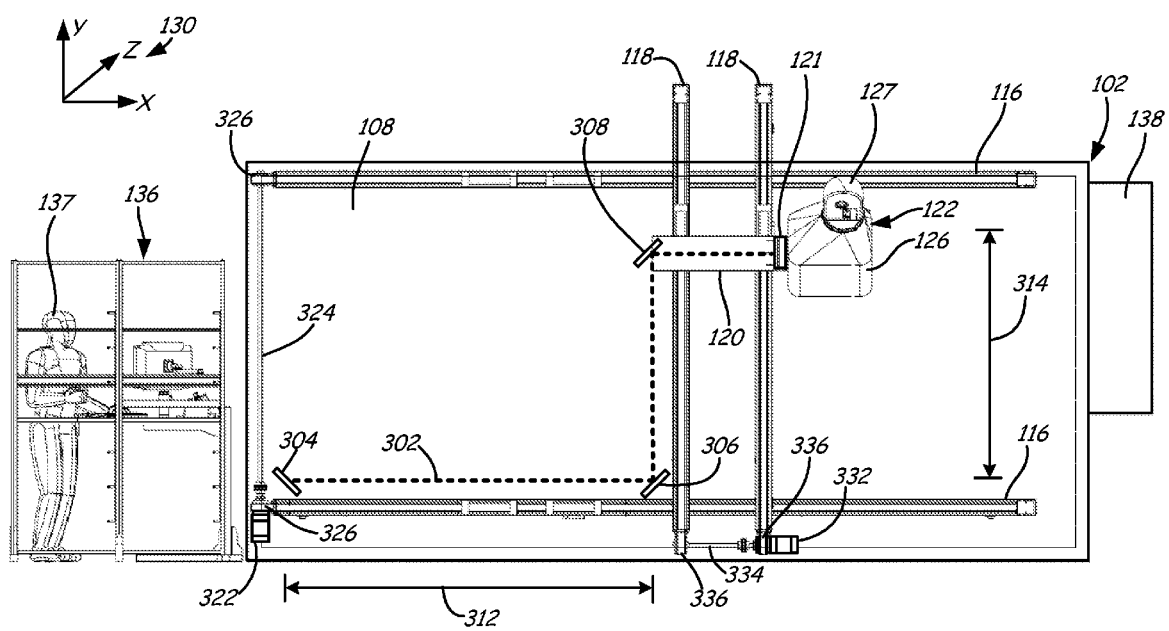
Figure 4:
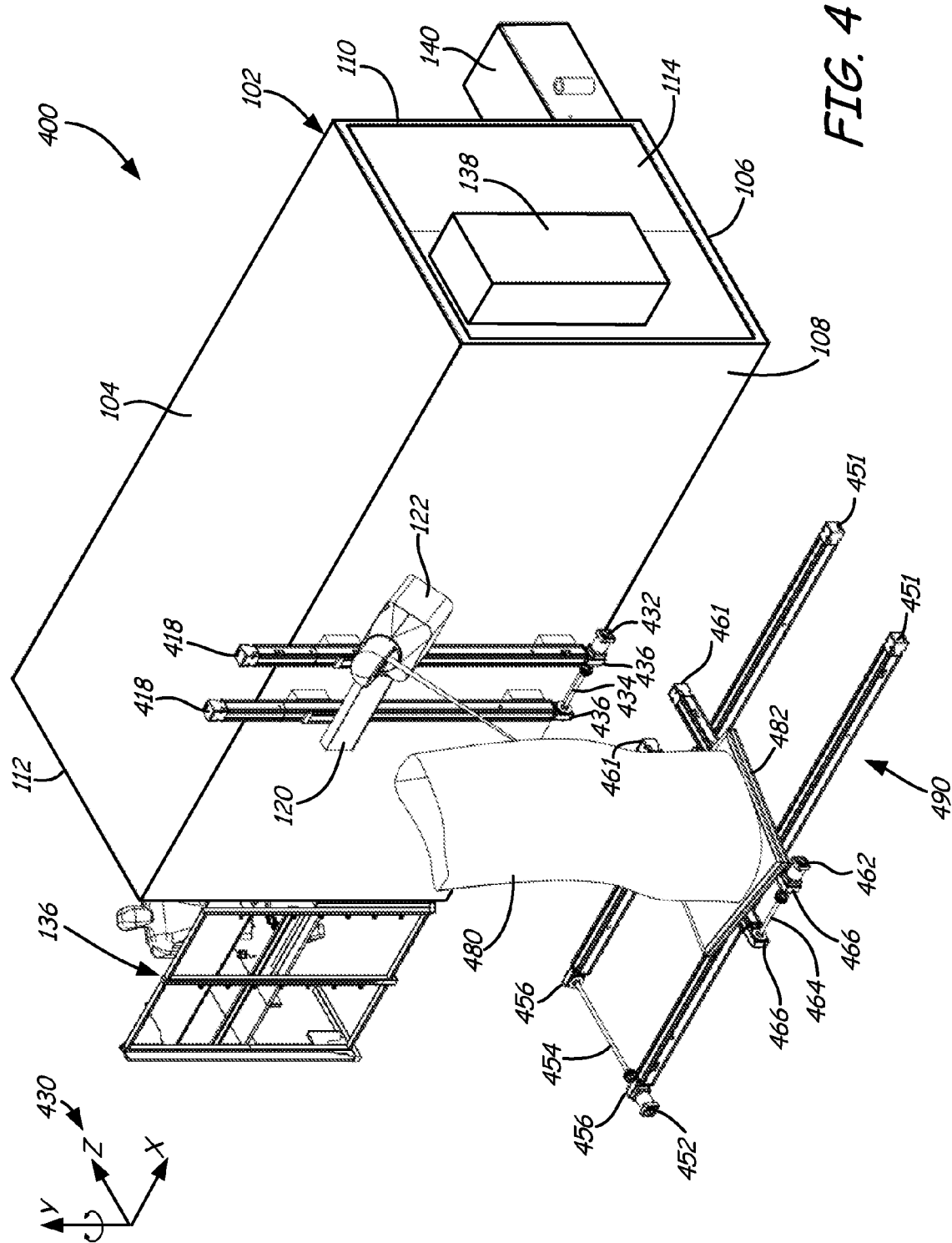
Figure 5:
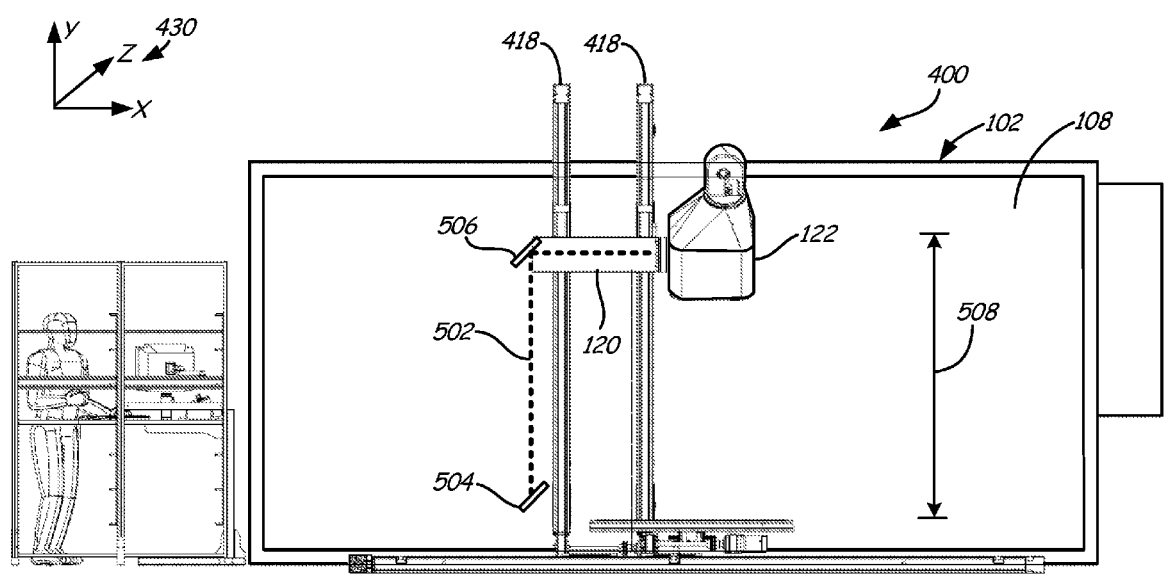
Figure 6:
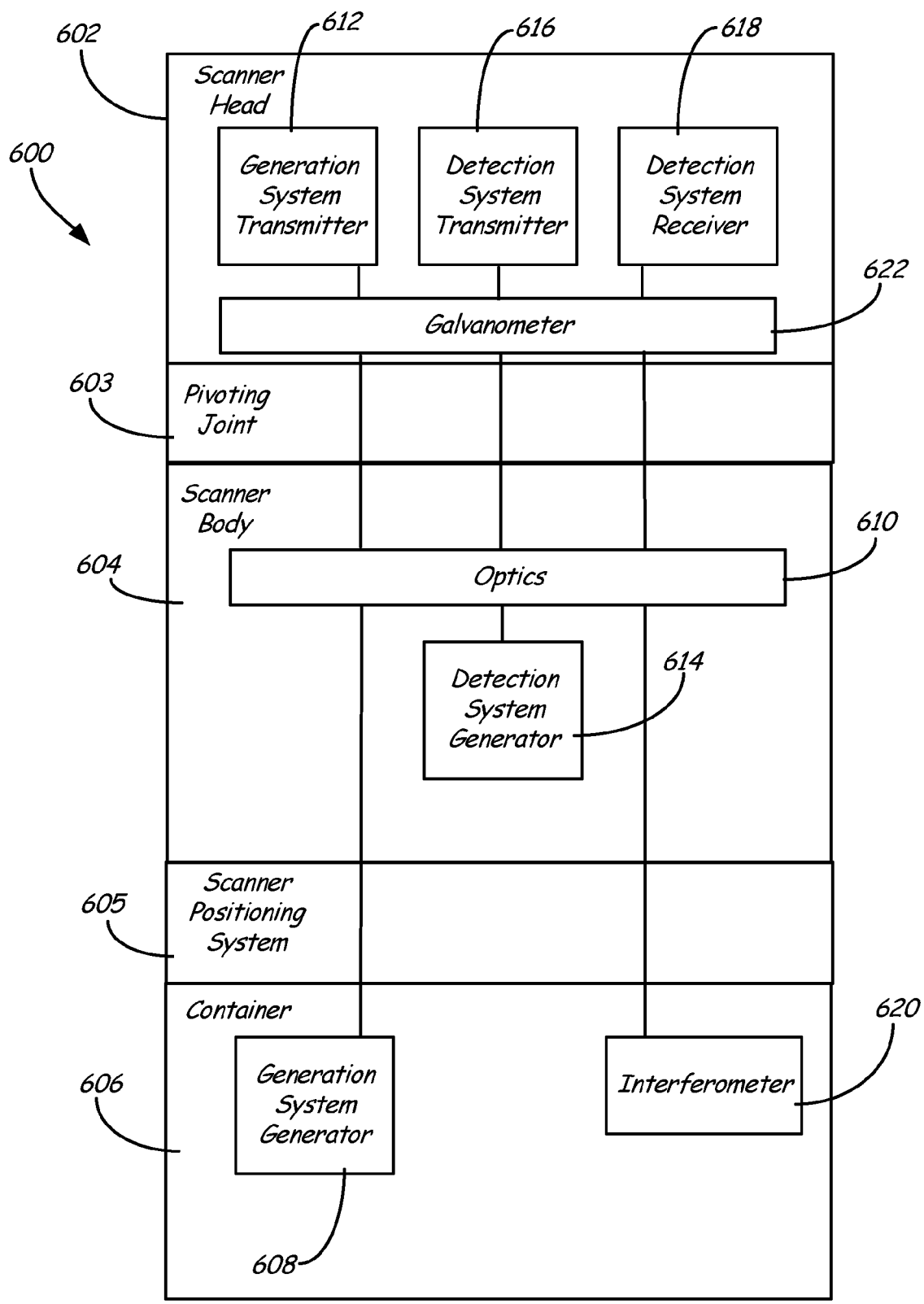
Figure 7:
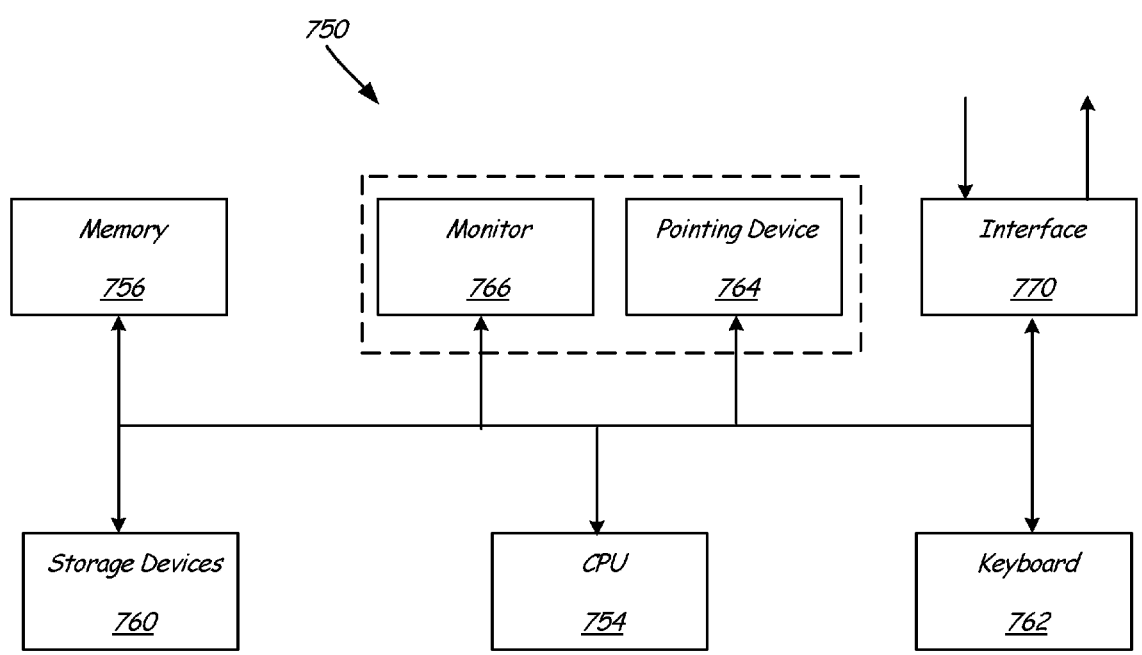

FIG. 1 is a perspective view of a containerized system.
FIG. 2 is a top down view of a containerized system.
FIG. 3 is a front view of a containerized system.
FIG. 4 is a perspective view of a containerized system having a reduced motion scanner.
FIG. 5 is a front view of a containerized system having a reduced motion scanner.
FIG. 6 is a schematic diagram of a containerized system.
FIG. 7 is a block diagram of a system controller that can be used in a containerized system.

DETAILED DESCRIPTION

Embodiments of the present disclosure include containerized systems. Containerized systems are illustratively advantageous in that they increase the portability of systems. This may be useful in reducing time and costs associated with delivering, installing, or relocating systems. For instance, in one embodiment, a containerized system can be shipped to a factory with the components of the system substantially set-up as needed for operating the system. The containerized system can then be placed in the factory and begin operating with relatively little effort needed in assembling the system or creating support structures for the system. Accordingly, containerized systems can be useful in rapidly installing a system in a factory or other setting. Similarly, containerized systems can also be useful in requiring less effort in removing or relocating a system, because the components can be moved/relocated without needing great amounts of disassembling or packaging.

Some examples of containerized systems that are described below and illustrated in the accompanying figures are shown as being associated with inspection systems (e.g. laser ultrasonic inspection systems). It should be noted however that embodiments of containerized systems are not limited to any particular type of system or any particular setting. For example, containerized systems can also be used in systems associated with welding, cutting, assembling, testing, painting, stamping, manufacturing, health care, etc. Accordingly, containerized systems can provide benefits such as reducing time and costs associated with delivering, installing, and relocating systems in a wide variety of different settings, and embodiments of containerized systems are thus not limited to only systems associated with inspecting.

FIG. 1 is a perspective view of one embodiment of a containerized system 100 that is implemented in an inspection setting. System 100 includes a portable container 102. Container 102 is illustratively moveable such that it, and any equipment included within it, can be relocated to a different location. In the specific example shown in the figure, container 102 has a rectangular prism shape and includes a top panel 104, a bottom panel 106, a front panel 108, a back panel 110, a first side panel 112, and a second side panel 114. Embodiments are not however limited to any particular shape or any number of panels, and embodiments include any shape and number of panels. For example, in other embodiments, a portable container 102 may be shaped as a cube, a pyramid, a cylinder, or any other three-dimensional shape. In certain embodiments, container 102 is formed as a modified shipping container, a custom design trailer, or any other type of shelter that can be moved from one location to another.

Portable container 102 illustratively supports one or more horizontal rails 116 and one or more vertical rails 118. A carriage 120 and a scanner 122 are mounted to vertical rails 116 such that they can be moved up and down along the y-axis shown by coordinate system 130. Movement of carriage 120 and scanner 122 along vertical rails 118 can be accomplished through drive assembly devices such as, but not limited to, actuators (e.g. hydraulic, pneumatic, or electric), electric linear motors, conveyor mechanisms, ball screw actuators, or pinion gears driven on racks provided on rails 118. Similarly, vertical rails 118 are mounted to horizontal rails 116 such that the vertical rails 118, carriage 120, and scanner 122 can be moved side to side along the x-axis shown by coordinate system 130. Movement of vertical rails 118 on horizontal rails 116 can be accomplished for example with any of the aforementioned devices or similar devices.

In one embodiment, scanner 122 transmits and receives electromagnetic waves 124 that are used to inspect an object 180. In the figure, electromagnetic waves 124 are illustrated as being a visible beam. This is done merely for illustration purposes only, and it should be recognized that electromagnetic waves 124 can include waves having any wavelengths (e.g. gamma rays, X rays, ultraviolet, visible spectrum, infrared, microwave, radio frequency, and long radio waves). Additionally, in other embodiments, scanner 122 does not necessarily need to transmit and receive electromagnetic waves, and scanner 122 instead transmits and/or receives other types of waves (e.g. sound waves, sonar, ultrasonic, subsonic) or materials (e.g. liquid, gas, particles, etc.).

In one particular advantageous embodiment, system 100 is a laser ultrasonic inspection system. In such a case, scanner 122 transmits a first electromagnetic wave (e.g. a wave generated by a $CO_2$ laser generator) to object 180. The first electromagnetic wave causes ultrasonic vibrations to occur within object 180. Scanner 122 then transmits a second electromagnetic wave (e.g. a wave generated by an Nd:YAG or Yb:YAG laser generator) that is reflected off from object 180 and is recaptured by scanner 122. As will be described in greater detail below, system 100 illustratively has a detection system that is able to detect changes in phase and/or frequency of the recaptured waves. The changes in phase and/or frequency can be used to identify defects in object 180. For instance, if object 180 is a composite material, system 100 can identify defects such as, but not limited to, inclusions, delamination, and porosity.

Scanner 122 optionally includes a body portion 126 and a head portion 128 that are connected together at a rotatable joint 127. Joint 127 enables scanner 122 to rotate beam 124 back and forth in the directions shown by double arrow 125. In one embodiment, for illustration purposes only and not by limitation, head portion 128 is able to rotate over a range of 180 degrees (e.g. +/−90°). Additionally, body portion 126 may be connected to carriage 120 through a rotatable joint 121 (shown and labeled in FIG. 3) such that scanner 122 is able to rotate beam 124 about the x-axis of coordinate system 130 as shown by double arrow 131. For instance, body portion 126 may be rotatable over a range of 135 degrees (e.g. 0 to 135°). Accordingly, scanner 122 is able to control the positioning of beam 124 by moving along horizontal rails 116, by moving along vertical rails 118, by rotating about joint 127, and by rotating about joint 121 (shown and labeled in FIG. 3).

Furthermore, scanner 122 may also optionally include a galvanometer or other controllable motion device that moves components with scanner head 128 along one or more axis. In one particular embodiment, scanner head 128 includes a two-dimensional galvanometer that moves the transmitted electromagnetic waves along two-dimensions. For instance, the two-dimensional galvanometer may have two scanning minors that enable movement of +/−10.5° mechanically and +/−21° optically along each of the two axes.

FIG. 1 also shows that the object being inspected 180 is held in place by an object holder 190. Object holder 190 may hold object 180 in a fixed position. Alternatively, object holder 190 may move object 180 in one or more directions (e.g. along the x-axis, y-axis, and/or z-axis 130) and/or may rotate object 180 about one or more axes (e.g. rotate about the x-axis, y-axis, and/or z-axis 130). Movement of object holder 190 can be accomplished through any type of device such as, but not limited to, actuators (e.g. hydraulic, pneumatic, or electric), electric linear motors, conveyor mechanisms, ball screw actuators, or pinion gears driven on racks. Additionally, movement of object holder 190 can be synchronized with movement of scanner 122 such that the system knows which location/area of object 180 is currently being scanned, and the scanner 122 is able to inspect all desired portion or every portion, if desired, of the object being inspected 180.

Container 102 may include one or more doors or panels 134 that provide access to any equipment within the container 102. Container 102 may also include one or more windows (not shown or none) to view the equipment within the container 102. Door 134 and the size of the container 102 are optionally sized to allow for a human being to enter the containerized system and move around in an upright fashion. Container 102 can include safety interlocks on its doors 134 and/or panels 104, 106, 108, 110, 112, and 114 such that no potentially dangerous electromagnetic waves are generated upon a door or panel being opened or removed. Similarly, any windows included within container 102 are optionally tinted or are made from a material such that no potentially dangerous electromagnetic waves (e.g. laser light) are emitted.

Containerized system 100 may also include an HVAC or air conditioning unit 138 and one or more heat exchange units or chillers 140. Air conditioning unit 138 illustratively controls the temperature and/or the humidity of air entering container 102. For instance, air conditioning unit 130 may cool, heat, dehumidify, and/or humidify air entering container 102. Air conditioning unit 138 may also include one or more filters to remove particulate and/or chemical contamination from entering container 102. Chillers 140 are illustratively used to cool one or more components of system 100. For instance, in one embodiment, system 100 includes three chillers 140. Two of the chillers 140 are used to control the temperature of an electromagnetic wave generator associated with a generation system (e.g. a $CO_2$ laser generator), and the third chiller 140 is used to control the temperature of an electromagnetic generator associated with a detection system (e.g. a Nd:YAG or Yb:YAG laser generator). Other embodiments may include any number of chillers 140 including none.

Finally with respect to FIG. 1, containerized system 100 may include an operations station 136. As will be described later in greater detail, operations station 136 illustratively includes equipment that enables a user 137 to control operations of the system. For instance, user 137 may use equipment within station 136 to perform real-time data analysis, to set-up the system to inspect an object, to review the results of an inspection, or to review any maintenance requirements.

FIG. 2 is a top down view of containerized system 100. In FIG. 2, the top panel 104 (shown and labeled in FIG. 1) has been removed from container 102 to illustrate some examples of components that may be included within container 102. In an embodiment, the components within container 102 are illustratively securely attached to or mounted within container 102 such that the container 102 and the components within it can be moved without any of the components being damaged or without any of the components needing to be uninstalled and reinstalled. Additionally, container 102 and the components within container 102 are illustratively secured in a fixed or stationary position such that they do not move during operations of the system (e.g. container 102 and generator 202 do not move while an object 180 is being inspected).

Container 102 optionally includes a generation system electromagnetic wave generator 202, a side arm catalyst unit 204, an interferometer 206, and electronics rack 208. Generator 202 illustratively generates waves that are used to cause ultrasonic vibrations in an object 180 that is being inspected. In one embodiment, generator 202 is a gas laser generator. For instance, generator 202 may be a carbon dioxide (i.e. $CO_2$) laser generator that generates electromagnetic waves having wavelengths centered at approximately 9.4 to 10.6 micrometers. In another embodiment, generator 202 is a mid-infrared generator that generates electromagnetic waves centered at approximately 3 to 8 micrometers. Embodiments of the present disclosure are not however limited to any particular type of generator 202 and illustratively include any type of generator that produces electromagnetic waves.

Sidearm catalyst unit 204 is utilized by generator 202 in generating electromagnetic waves. In one embodiment, catalyst unit 204 is a carbon dioxide catalyst that helps to regenerate a carbon dioxide laser gas mix. Catalyst unit 204 may however include other types of catalyst as needed to support the generation of electromagnetic waves by generator 202. Additionally, catalyst unit 120 does not necessarily need to include any type of catalyst and may instead be another type of supporting equipment that helps generator 202 generate waves.

Interferometer 206 illustratively receives electromagnetic waves reflected or scattered from the object 180 being inspected. For instance, as previously mentioned, in one embodiment, scanner 122 transmits a first electromagnetic wave (e.g. a wave generated by generator 202) to object 180. The first electromagnetic wave causes ultrasonic vibrations to occur within object 180. Scanner 122 then transmits a second electromagnetic wave (e.g. a wave generated by an Nd:YAG or Yb:YAG laser generator) that is reflected off from object 180 and is recaptured by scanner 122. The recaptured waves are transmitted to interferometer 206 that is able to detect changes in phase and/or frequency of the recaptured waves. The changes in phase and/or frequency can be used to identify defects in object 180 such as, but not limited to, inclusions, delamination, and porosity.

In one specific example, for illustration purposes only and not by limitation, interferometer 206 is a confocal Fabry-Perot interferometer. The Fabry-Perot interferometer has sensitivity for frequencies between 0.5 to 15 megahertz and is able to handle rough surfaces. The Fabry-Perot interferometer is a homodyne interferometer having two minors that form a resonant cavity that analyzes the phase and the frequency of the reflected wave. In one implementation, the Fabry-Perot interferometer has two spherical minors spaced approximately 1 meter apart, and interferometer 206 outputs a wave that reflects back and forth approximately ten to one hundred times within the cavity of the interferometer 206. This implementation can be configured to reject common-node amplitude noise produced by differences/imperfections in wavelengths and/or frequencies of the wave that is being reflected from the object 180 that is being inspected.

Electronics rack 208 includes any type of electronics that are needed or are useful in supporting the operations of containerized system 100. Some examples of electronics that may be included are a computing system (e.g. PC or server), a data archive or database for storing and retrieving inspection information, defect detection analysis hardware and/or software, an uninterrupted power supply, communications interfaces (e.g. wireless transmitter/receiver), one or more controllers, and/or power supplies/conditioners. In one embodiment, a computing system of electronics rack 208 includes a data acquisition and control subsystem, a data visualization subsystem, and a data management subsystem. Waveforms (e.g. ultrasonic waveforms from interferometer 206) are digitally captured, processed, and stored while the inspection area/point is indexed over the surface of the object 180 that is being inspected (e.g. a composite surface). Real-time data analysis and visualization tools are available to the user 137 that may decrease time required for inspection and/or analysis processes. The data management is optionally performed with an automated archival system and a database such as, but not limited to, a SQL server database.

In addition to the components included within container 102, system 100 may also include one or more components outside of or partially outside of container 102. These components may be securely attached to container 102 such that they can be moved along with the container 102, or alternatively, the components may be detachable such that they can be removed before moving. Some examples of outside or partially outside components include the air conditioning unit 138 and the one or more chillers 140 discussed above. The outside components may also include one or more gas tanks 210. Gas tanks 210 supply gases to components of system 100 such as to electromagnetic wave generator 202. For instance, tanks 210 may include carbon dioxide (i.e. $CO_2$), nitrogen ($N_2$), hydrogen ($H_2$), carbon monoxide (CO) and helium (He) gases that are used as gas supplies for a $CO_2$ laser generator. Embodiments are of course not limited to any particular implementation and illustratively include any number and types of gases including none.

It should be noted that, in an embodiment, container 102 includes one or more apertures and/or connection points such that gases, cooling lines, and air (e.g. from gas tanks 210, chillers 140, and/or A/C unit 138) may be exchanged between outside components and the components within container 102. These apertures and/or connection points are illustratively sealed such that no dangerous electromagnetic waves escape from container 102 and such that the connections can be at least relatively easily connected/disconnected so that containerized system 100 is moveable.

As shown in FIG. 2, containerized system 100 optionally includes a work cell 220 that surrounds or partially surrounds the object 180 that is being inspected. The walls or panels 222 of the cell can be of a permanent nature or, in a particularly advantageous form, the walls or panels 222 can be of a temporary or moveable form. In addition to the side walls 222, work cell 220 may also include one or both of a bottom/floor panel 240 and a top/ceiling panel 242. In the figure, the top/ceiling panel 242 is illustrated as being a broken surface so that the components within work cell 220 can be seen. It should be noted that the top/ceiling panel 242 is illustratively a continuous surface that fully covers the entirety of the top of the work cell 220. It should also be noted that embodiments of work cell 220 are not limited to any particular shape. For instance, although the particular example of work cell 220 shown in the figure has four to six panels that form a rectangular prism shape, embodiments of work cells 220 may include any number of panels to form any shape. Furthermore, as shown in FIG. 2, the front panel 108 of container 102 in one embodiment is separate from (i.e. does not form a part of) work cell 220. In another embodiment, container 102 and work cell 220 share one or more walls. For instance, front panel 108 can be used to form one of the walls of work cell 220, or one of the work cell panels 222 can be used to form one of the walls of container 102.

In the embodiment shown in FIG. 2, panels 222 are illustratively joined together along the vertices 232 of the work cell 220. In one embodiment, panels 222 are joined together utilizing any suitable fasteners. Additionally, panels 222 may optionally include seals 234 along the intersections of adjoining panels 222. Accordingly, panels 222 can be joined together in such a manner as to prevent electromagnetic waves from escaping the interior portion of work cell 220. The bottom/floor panel 240 and/or the top/ceiling panel 242 can similarly be joined to panels 222 utilizing suitable fasteners and/or seals to prevent electromagnetic waves from escaping the interior portion of work cell 220.

Work cell 220 may also have one or more doors/access panels 224 and/or one or more windows (e.g. laser safe windows). The work cell 220 can illustratively include safety features that are the same or similar to those of container 102. For instance, work cell 220 may include interlocks on its panels and/or doors to de-energize equipment such that dangerous electromagnetic waves cannot be generated if the interlocks are opened. Also for instance, the cell 220 and any windows may be tinted or made of such a material such that dangerous electromagnetic waves cannot be emitted from the work cell 220. In one embodiment, a work cell 220 optionally includes one or more laser status indicators. For instance, a work cell 220 may include a laser status indicator at each entrance. The status indicator could for example indicate to a user whether or not a laser is active or not. This could be useful in preventing a user from walking into a work cell 220 when the laser is turned on. Additionally, the doors to the work cell 220 may be interlocked such that the laser is de-activated (i.e. waves are not generated) when a door is opened.

Furthermore, in one embodiment, the work cell 220 can be constructed of modular panels (e.g. panels 222, 240, and/or 242) that are shipped with the container 102 and that are designed to be attached thereto and/or to each other. The modular panels may be rigid panels, or alternatively, the panels may be flexible panels (e.g. like a curtain, etc.).

Operations station 136 provides an area in which a user 137 can operate the components of system 100. Station 136 illustratively includes a monitor and/or input devices (e.g. scrollball, keyboard, mouse, touchscreen) that communicates with electronics (e.g. a computer) within electronics rack 208. The communications may be wireless or may be through a wired connection through an aperture in container 102. In an embodiment, user 137 can utilize the equipment within station 136 to perform real-time data analysis, visualization, and/or any of the other tasks discussed above. An operator can also illustratively utilize the equipment within the station to set-up the system to inspect an object, to review the results of an inspection, to review/monitor any maintenance requirements, etc.

System 100 also optionally includes a wireless handheld control terminal 226 that is wirelessly communicatively coupled to one or more of electronics rack 208 and/or equipment within operations station 136. In an embodiment, wireless handheld control terminal 226 includes a reader (e.g. an optical barcode reader or an RFID reader) that reads an identifier 228 (e.g. a one-dimensional barcode, a two-dimensional barcode, or an RFID tag) on an object 180 that is to be inspected. Handheld control terminal 226 illustratively has a graphical interface that provides instructions and/or feedback to a scanner. For instance, the graphical interface can show whether a barcode was or was not successfully read. Handheld control terminal 226 may be implemented utilizing a computing device such as, but not limited to, a laptop computer, a netbook, a tablet computer, or a smartphone. Handheld control terminal 226 is not however limited to any particular device and can be implemented utilizing any suitable device.

Handheld control terminal 226 illustratively reads the identifier 228 on the object 180 and then attempts to retrieve positioning information for that part. For example, the object 180 may have been previously taught to the system such that the system knows the coordinates/dimensions of the part (e.g. coordinates/dimensions stored in a database of electronics rack 208). If the object has been taught to the system, the system continues with the inspection process. If the object has not been taught to the system (e.g. the system does not have coordinate/dimension information for the object), then the terminal 226 allows the user 137 to teach the object 180 and store the information to a computing device (e.g. a database within electronics rack 208). The stored teach information can then be recalled as necessary. For instance, the stored teach information can be recalled the next time when an object having the same or a similar shape is inspected.

Handheld control terminal 226 may also include other features. In one embodiment, terminal 226 provides capabilities to control robots/motion systems within system 100, to control electromagnetic wave generators (e.g. generator 202), to control interferometer 206, and to control any other components that may be included within system 100 and/or communicatively coupled to system 100.

FIG. 3 is a front view of containerized system 100. The figure shows one embodiment of a mirror configuration that can be used for example to direct an electromagnetic wave 302 from a generator (e.g. generator 202 in FIG. 2) to scanner 122. In an embodiment, an electromagnetic wave 302 travels outward from container 102 along the z-axis shown in coordinate system 130 through a suitable aperture with or without a covering allowing transmission there through. The wave 302 is then redirected (e.g. reflected) by a stationary mirror 304 along the x-axis 130 towards a first travelling mirror 306. First travelling mirror 306 is illustratively attached to vertical rails 118 such that it moves along with the vertical rails 118. For instance, FIG. 3 shows a distance 312 that separates mirrors 304 and 306. Distance 312 increases or decreases as vertical rails 118 move along horizontal rails 116.

From the first travelling mirror 306, wave 302 is then directed upwards along the y-axis 130 towards a second travelling mirror 308. Second travelling mirror 308 is illustratively attached to carriage 120 such that it moves along with the carriage 120. For instance, FIG. 3 shows a distance 314 that separates mirrors 306 and 308. Distance 314 increases or decreases as carriage 120 moves along vertical rails 118. Wave 302 is then directed by mirror 308 along the x-axis 130 towards scanner 122. Carriage 120 is optionally hollow or has an aperture that enables wave 302 to travel from mirror 308 to scanner 122.

In one embodiment, wave 302 is a two and a half inch diameter beam from a carbon dioxide laser. Embodiments are not however limited to any particular type or size of electromagnetic waves and can include any type and size of electromagnetic wave. Additionally, it should be noted that mirrors 304, 306, and 308 do not necessarily need to be mirrors. Mirrors 304, 306, and 308 can for instance be any type of redirecting device. For example, one or more of mirrors 304, 306, and 308 could be implemented using a prism instead of a mirror. Furthermore, embodiments of the present disclosure are not limited to any particular configuration of mirrors/redirecting devices and can include other configurations as necessary to redirect a wave from a generator to scanner 122.

FIG. 3 also shows that system 100 may include a first motor 322 attached to one of the horizontal rails 116, and a second motor 332 attached to one of the vertical rails 118. First motor 322 has a rotatable output shaft 324. Motor 322 and shaft 324 rotate bands 326 that run along the horizontal rails 116 and that are attached to vertical rails 118. Accordingly, as motor 322 and shaft 324 rotate clockwise or counterclockwise, bands 326 move vertical rails 118 along horizontal rails 116. Similarly, second motor 332 has a rotatable output shaft 334. Motor 332 and shaft 334 rotate bands 336 that run along the vertical rails 118 and that are attached to carriage 120. Accordingly, as motor 332 and shaft 334 rotate clockwise or counterclockwise, bands 336 move carriage 120 along vertical rails 118.

Embodiments of the present disclosure are not however limited to any particular methods of supplying motion or positioning capabilities to scanner 122. For instance, as previously mentioned, embodiments may utilize actuators (e.g. hydraulic, pneumatic, or electric), electric linear motors, conveyor mechanisms, ball screw actuators, or pinion gears driven on racks provided on rails. Furthermore, system 100 does not necessarily need to have any rails. For example, in another embodiment, scanner 122 is positioned utilizing one or more multi-axes robots or any other suitable device. It should also be noted that the rails, multi-axes robot, etc. that are used to position scanner 122, do not necessarily need to be supported by the container 102. In another embodiment, the rails, multi-axes robot, etc. are self-supporting and do not need to be attached to or supported by container 102. In yet another embodiment, the rails, multi-axes robot, etc. are supported by one or more walls of a work cell (e.g. walls 222 of work cell 220 in FIG. 2). Accordingly, embodiments provide flexibility in which motion can be provided to scanner 122.

Embodiments of the present disclosure are also not limited to any particular layout. For instance, in the examples shown in FIGS. 1 and 2, the object 180 that is being inspected is outside of the container 102. In another embodiment, the inspection of objects is performed within the container 102. In such a case, container 102 is sized such that components such as scanner 122, object holder 190, and rails 116/118 can be placed within the container 102. Additionally, an operations station (e.g. station 136 in FIGS. 1 and 2), can also be located within a container 102, and the container 102 may optionally have one or more suitable partitions to isolate the operations station from any generation system (e.g. generator 202 in FIG. 2) and/or object inspection area. Furthermore, any supporting components such as gas tanks 210, chillers 140, HVAC unit 138, may also be placed within container 102. Therefore, embodiments of the present disclosure include different options for layout configurations, which may provide further flexibility for installing, relocating, and/or operating a containerized system.

Another possible layout, for illustration purposes only and not by limitation, includes placing everything within the moveable container. For example, the operations station, the work cell (i.e. object inspection area), supporting components (e.g. gas tanks, chillers, etc.), the scanner, and the scanner positioning system are illustratively all placed within a moveable container. In another possible layout, the operations station (e.g. station 136 in FIG. 1) is placed within a moveable container, but the work cell (e.g. the object inspection area) is placed outside of the moveable container. This other layouts may provide further options for incorporating a containerized system in an operating environment.

Additionally, embodiments of the present disclosure are not limited to any particular sizes. For instance, although illustrated herein with a container 102 that is of suitable size for containing a human within, other embodiments can include a housing of size to contain one or more of the components herein described (e.g. object 180 and/or generator 202 in FIG. 2), but not be of size to accommodate a human. This construction, of whatever size, is particularly beneficial for containerized systems herein described.

FIG. 4 is a perspective view of another embodiment of a containerized system, system 400. Similar to system 100 shown in FIGS. 1-3, system 400 illustratively includes a container 102 having a top panel 104, a bottom panel 106, a front panel 108, a back panel 110, and side panels 112/114. System 400 may also illustratively include a carriage 120, a scanner 122, an HVAC unit 138, one or more chillers 140, and an operations station 136. Additionally, system 400 optionally includes any one or more features or combinations of features described above or shown in the accompanying figures.

In one embodiment, system 400 differs from system 100 in the method and components used for positioning scanner 122 and the object 480 that is being inspected. For instance, in FIGS. 1-3, system 100 illustratively includes horizontal rails 116 supported by front panel 108. System 400 optionally does not include any horizontal rails on its front panel 108. Instead, front panel 108 in system 400 illustratively only includes one or more vertical rails 418. In one embodiment, system 400 includes a motor 432 that is attached to one of the vertical rails 418 and that has a rotatable output shaft 434. Motor 432 and shaft 434 rotate bands 436 that run along the vertical rails 418 and that are attached to carriage 120. Accordingly, as motor 432 and shaft 434 rotate clockwise or counterclockwise, bands 436 move carriage 120 and scanner 122 up and down along the y-axis shown by coordinate system 430.

Object holder 490 may also include one or more rails for providing motion to the object 480 that is being inspected. In one embodiment, object holder 490 includes one or more rails 451 that run along the x-axis of coordinate system 430, and one or more rails 461 that run along the z-axis of coordinate system 430. A motor 452 having a rotatable output shaft 454 is attached to one of the rails 451. Motor 452 and shaft 454 rotate bands 456 that run along rails 451 and that are attached to rails 461. Accordingly, as motor 452 and shaft 454 rotate clockwise or counterclockwise, bands 456 move the object holder platform 482, and thus object 480, side to side along the x-axis of coordinate system 430.

Similarly, a motor 462 having a rotatable output shaft 464 is illustratively attached to one of the rails 461. Motor 462 and shaft 464 rotate bands 466 that run along rails 461 and that are attached to object holder platform 482. Accordingly, as motor 462 and shaft 464 rotate clockwise or counterclockwise, bands 466 move the object holder platform 482, and thus object 480, back and forth along the z-axis of coordinate system 430. Additionally, in one embodiment, object holder platform 482 may be rotatable about the y-axis of coordinate system 430 by separately adjusting bands 466.

Embodiments of the present disclosure are not however limited to any particular methods or components for moving or positioning scanner 122 and/or object holder platform 482. For instance, movement of scanner 122 and/or platform 482 can be accomplished through any type of device such as, but not limited to, actuators (e.g. hydraulic, pneumatic, or electric), electric linear motors, conveyor mechanisms, ball screw actuators, or pinion gears driven on racks. Furthermore, movement of object holder 490 can be synchronized with movement of scanner 122 such that the system knows which location/area of object 480 is currently being scanned, and the scanner 122 is able to inspect every portion of the object being inspected 480.

FIG. 5 is a front view of containerized system 400. The figure shows one embodiment of a minor configuration that can be used for example to direct an electromagnetic wave 502 from a generator (e.g. generator 202 in FIG. 2) to scanner 122. In an embodiment, an electromagnetic wave 502 travels outward from container 102 along the z-axis of coordinate system 430. The wave 502 is then redirected (e.g. reflected) by a stationary mirror 504 along the y-axis 430 towards a travelling mirror 506. Travelling mirror 506 is illustratively attached to carriage 120 such that it moves along with the carriage 120. For instance, FIG. 5 shows a distance 508 that separates mirrors 504 and 506. Distance 508 increases or decreases as carriage 120 moves along vertical rails 418.

From the travelling mirror 506, wave 502 is then directed along the x-axis 430 towards scanner 122. Carriage 120 is optionally hollow or has an aperture that enables wave 502 to travel from minor 506 to scanner 122. It should be noted that mirrors 504 and 506 do not necessarily need to be minors. Mirrors 504 and 506 can for instance be any type of redirecting device. For example, one or more of minors 504 and 506 could be implemented using a prism instead of a minor. Furthermore, embodiments of the present disclosure are not limited to any particular configuration of mirrors/redirecting devices and can include other configurations as necessary to redirect a wave from a generator to scanner 122.

FIG. 6 is a schematic block diagram illustrating some components that may be included within a containerized system, system 600. System 600 includes a scanner head 602 that is connected to a scanner body 604 through a pivot joint 603. System 600 also includes a container 606 that is connected to the scanner body 604 through a scanner positioning system 605.

In an embodiment, system 600 includes a generation system that generates a first electromagnetic wave and a detection system that generates a second magnetic wave. The first electromagnetic wave is illustratively generated by a generation system generator 608. Generator 608 may be a gas laser generator (e.g. a $CO_2$ generator) or any other type of generator (e.g. gas laser generator, solid state laser generator, etc.). As shown in the figure, generator 608 is optionally located within container 606. Generator 608 could however be located at other locations within the system such as within scanner body 604. From generator 608, the generation system electromagnetic wave is illustratively transferred through optics 610 within scanner body 610 to a generation system transmitter 612 in scanner head 602. From transmitter 612, the generation system electromagnetic wave is illustratively directed to an object that is being inspected (e.g. a composite material). The generation system wave in one embodiment causes ultrasonic vibrations to occur within the object.

Next, a second electromagnetic wave is illustratively generated by a detection system generator 614. Generator 614 may be a solid state generator (e.g. a Nd:YAG or Yb:YAG laser generator) or any other type of generator (e.g. a gas laser generator, etc.). As shown in the figure, generator 614 is optionally located within the scanner body 604. Generator 614 could however be located at other locations within the system such as within container 606. From generator 614, the detection system electromagnetic wave is illustratively transferred through optics 610 within scanner body 610 to a detection system transmitter 616 in scanner head 602. From transmitter 616, the detection system electromagnetic wave is illustratively directed to the object being inspected.

The detection system electromagnetic wave is then reflected or redirected by the object being inspected, and is recaptured or received by the detection system receiver 618 in scanner head 602. The recaptured detection system wave is then optionally transferred through optics 610 in scanner body 604 to an interferometer 620 in container 602. Interferometer 620 is illustratively able to detect changes in phase and/or frequency of the recaptured waves, and can use those detected changes to identify defects in the object being inspected.

FIG. 6 further shows that scanner head 602 may include a galvanometer 622 that can be used to further position generation system transmitter 612, detection system transmitter 616, and/or detection system receiver 618. In one embodiment, galvanometer 622 is a two-dimensional galvanometer that moves the transmitted electromagnetic waves along two-dimensions. For instance, the two-dimensional galvanometer may have two scanning mirrors that enable movement of +/−10.5° mechanically and +/−21° optically along each of the two axes.

Scanner head 602 and/or scanner body 604 may also contain any other components that may be necessary or desirable. For instance, scanner head 602 and body 604 may include additional electrical, fiber optic, or other type of cabling. Scanner head 602 and body 604 may also include any number of additional optical or mechanical components for transmitting or redirecting electromagnetic waves. Furthermore, embodiments may include safety covers or dust covers for any of the electromagnetic waves.

FIG. 7 is a block diagram of one example of a system controller 750 that may be used in a containerized system (e.g. electronics rack 208, operations station 136, and/or handheld control terminal 226 in FIG. 2). System controller 750 illustrated in FIG. 7 comprises a conventional computer having a central processing unit (CPU) 754, memory 756, and a system bus 758, which couples various system components, including memory 756 to the CPU 754. The system bus 758 may be any of several types of bus structures including a memory bus or a memory controller, a peripheral bus, and a local bus using any of a variety of bus architectures. The memory 756 includes read only memory (ROM) and random access memory (RAM). A basic input/output (BIOS) containing the basic routine that helps to transfer information between elements within the controller 750, such as during start-up, is stored in ROM. Storage devices 760, such as a magnetic, optical, solid state, or polymer-based storage systems are coupled to the system bus 758 and are used for storage of programs and data. Commonly, programs are loaded into memory 756 from at least one of the storage devices 760 with or without accompanying data.

Input devices such as a keyboard 762, pointing device (e.g. mouse) 764, or the like, allow the user to provide commands to controller 750. A monitor 766 or other type of output device is further connected to the system bus 758 via a suitable interface and provides feedback to the user. If the monitor 766 is a touch screen, the pointing device 764 can be incorporated therewith. The monitor 766 and typically an input pointing device 764 such as mouse together with corresponding software drivers form an interface 770 (e.g. a graphical user interface) for controller 750. Interface(s) 770 allow communication between system controller 750 and other system components. Interface(s) 770 also represent circuitry used to send and receive signals. Commonly, such circuitry comprises digital-to-analog (D/A) and analog-to-digital (A/D) converters as is well known in the art.

As has been described above and shown in the accompanying figures, embodiments of the present disclosure include containerized systems. Containerized systems are illustratively advantageous in that they increase the portability of systems. This may be useful in reducing time and costs associated with delivering, installing, or relocating systems. For instance, in one embodiment, a containerized system can be shipped to a factory with the components of the system substantially set-up as needed for operating the system. The containerized system can then be placed in the factory and begin operating with relatively little effort needed in assembling the system or creating support structures for the system. Accordingly, containerized systems can be useful in rapidly installing a system in a factory or other setting. Similarly, containerized systems can also be useful in requiring less effort in removing or relocating a system, because the components can be moved/relocated without needing great amounts of disassembling or packaging.

Finally, although the subject matter has been described in language specific to structural features and/or methodological acts, it is to be understood that the subject matter defined in the appended claims is not necessarily limited to the specific features or acts described above as has been determined by the courts. Rather, the specific features and acts described above are disclosed as example forms of implementing the claims.

What is claimed is:

1. A containerized system comprising:
    a moveable three-dimensional container;
    a first generator that is located within the container;
    a second generator that is located outside of the container; and
    a scanner that is mechanically supported by the container and that transmits waves received from the first and the second generators
    a stationary mirror that is attached to a fixed position on an outer surface of the container;
    a moving mirror that moves with respect to the outer surface of the container; and
    wherein the scanner, the stationary mirror and the moving mirror are configured to receive electromagnetic waves that are generated by the first generator and that are reflected by the stationary and the moving mirror.

2. The system of claim 1, wherein one or more rails are connected to the outside of the container, and wherein the scanner is moveable along the one or more rails.

3. The system of claim 1, wherein the scanner is positioned utilizing a multi-axes arm that is mechanically supported by the container.

4. The system of claim 1, and further comprising:
    an interferometer that is located within the container.

5. The system of claim 1, and further comprising:
    an electronics rack that is located within the container.

6. The system of claim 1, and further comprising:
    an air conditioning unit that is mechanically supported by the container.

7. The system of claim 1, and further comprising:
    modular panels configured to be connected to each other to form a work cell.

8. The system of claim 7, wherein at least one of the modular panels is configured to be connected to the container to form a portion of the work cell.

9. The system of claim 7, wherein the modular panels are configured to form a work cell formed separately from the container.

10. The system of claim 1, and further comprising:
    a second moving mirror that moves with respect to the outer surface of the container and that reflects electromagnetic waves from the stationary mirror to the moving mirror.

11. The system of claim 1, wherein the container comprises a modified shipping container.

12. The system of claim 1, wherein the container comprises a custom design trailer.

13. The system of claim 1, wherein the container includes one or more apertures for transferring gas to the first generator.

14. The system of claim 1, wherein the container includes one or more apertures for transferring heat exchange fluids to the first generator.

15. The system of claim 1, wherein one or more panels of the container have interlocks configured to power down the first generator.

16. The system of claim 1, wherein the scanner is carried by a carriage that moves the scanner with respect to the outer surface of the container.

17. The system of claim 1 wherein the first generator is a gas laser generator, wherein the second generator is a solid state laser generator, and wherein the scanner is configured to transmit electromagnetic waves received from the gas laser generator and the solid state laser generator.

18. The system of claim 17, wherein the gas laser generator is a carbon dioxide laser generator.

19. The system of claim 17, wherein the solid state laser generator is a Nd:YAG laser generator.

20. The system of claim 17, wherein the solid state laser generator is a Yb:YAG laser generator.

21. The system of claim 17, and further comprising:
    modular panels configured to be connected to each other to form a work cell.

* * * * *